United States Patent
Chu

(10) Patent No.: US 8,545,388 B2
(45) Date of Patent: Oct. 1, 2013

(54) APPARATUS AND METHOD FOR UTERINE PRESERVATION

(75) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 498 days.

(21) Appl. No.: 12/482,568

(22) Filed: Jun. 11, 2009

(65) Prior Publication Data
US 2009/0319053 A1 Dec. 24, 2009

Related U.S. Application Data

(60) Provisional application No. 61/074,305, filed on Jun. 20, 2008.

(51) Int. Cl.
*A61F 2/00* (2006.01)
*A61F 13/00* (2006.01)

(52) U.S. Cl.
USPC ............... 600/37; 600/7; 623/23.64; 606/151

(58) Field of Classification Search
USPC ............... 600/37, 7; 623/23.64; 606/151
See application file for complete search history.

(56) References Cited

U.S. PATENT DOCUMENTS

| | | | | |
|---|---|---|---|---|
| 7,070,558 B2 * | 7/2006 | Gellman et al. | ................ | 600/37 |
| 7,156,858 B2 * | 1/2007 | Schuldt-Hempe et al. | ... | 606/151 |
| 7,594,921 B2 * | 9/2009 | Browning | .................... | 606/151 |
| 2002/0103542 A1 * | 8/2002 | Bilbo | ......................... | 623/23.72 |
| 2004/0039453 A1 | 2/2004 | Anderson et al. | | |
| 2004/0172048 A1 * | 9/2004 | Browning | .................... | 606/151 |
| 2005/0038452 A1 * | 2/2005 | Chu | .............................. | 606/151 |
| 2006/0229493 A1 * | 10/2006 | Weiser et al. | .................... | 600/37 |
| 2006/0229596 A1 * | 10/2006 | Weiser et al. | .................... | 606/37 |
| 2006/0258898 A1 | 11/2006 | Montpetit et al. | | |
| 2007/0021649 A1 * | 1/2007 | Nowlin et al. | .................. | 600/30 |
| 2007/0055095 A1 * | 3/2007 | Chu et al. | ......................... | 600/37 |
| 2007/0123915 A1 * | 5/2007 | Kammerer et al. | ........... | 606/151 |
| 2008/0039678 A1 | 2/2008 | Montpetit et al. | | |
| 2008/0167729 A1 * | 7/2008 | Nelson et al. | .............. | 623/23.72 |
| 2008/0177132 A1 * | 7/2008 | Alinsod et al. | ................. | 600/37 |

FOREIGN PATENT DOCUMENTS

WO  WO 2006/045042 A1  4/2006
WO  WO 2007/118260 A1  10/2007

OTHER PUBLICATIONS

International Preliminary Report on Patentability for PCT Patent Application No. PCT/US2009/047617, mailed Jan. 6, 2011, 9 pages.
International Search Report and Written Opinion for International Application No. PCT/US09/047617, mailed Sep. 18, 2009, 11 pages.

* cited by examiner

*Primary Examiner* — Christine Matthews
*Assistant Examiner* — Sunita Reddy

(57) ABSTRACT

In one embodiment, an implant includes a first portion having a shape and configured to support a tissue within the body of a patient. Markings disposed on the first portion indicate a portion of the implant to be removed for resizing the first portion such that the first portion after the resizing has a shape substantially similar to the shape of the first portion before the resizing.

20 Claims, 5 Drawing Sheets

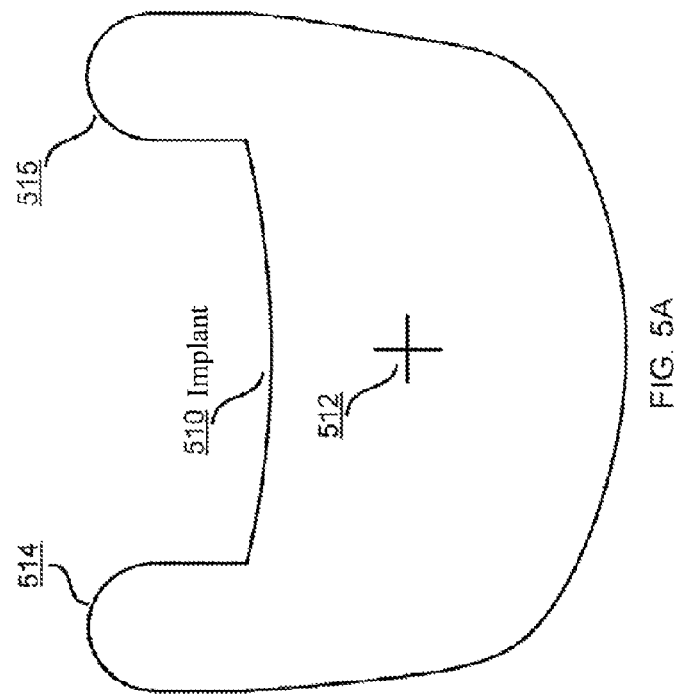
FIG. 5A
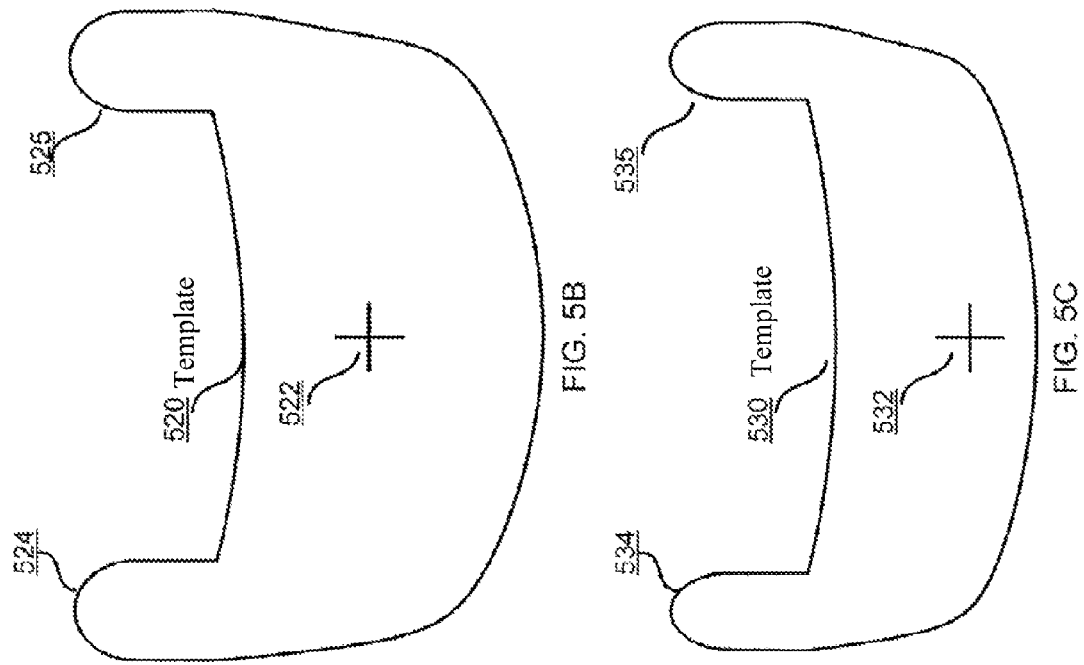
FIG. 5B
FIG. 5C

APPARATUS AND METHOD FOR UTERINE PRESERVATION

This application claims priority under 35 U.S.C. §119(e) to U.S. Provisional Patent Application No. 61/074,305, entitled "Apparatus and Method for Uterine Preservation," filed on Jun. 20, 2008.

BACKGROUND

The invention relates generally to medical devices, and in particular to an apparatus for treating various pelvic dysfunctions including procedures to repair uterine prolapse, cystoceles, rectoceles, and vaginal vault prolapse.

A vaginal prolapse can be due to age or other factors and typically results in one of three types of prolapse: hysterocele, cystocele, and rectocele. A hysterocele occurs when the uterus descends into the vagina and is often treated with a hysterectomy followed by a vaginal vault suspension. A cystocele prolapse occurs when the bladder bulges or descends into the vagina and a rectocele occurs when the rectum bulges or descends into the vagina. It is common for more than one type of prolapse to occur at the same time. Treatment of vaginal vault prolapse, including a vaginal prolapse due to a hysterocele, can include a suturing procedure or the use of an implant for support or suspension.

Another procedure to treat a prolapse caused by a hysterocele is to perform a hysterectomy. Many patients, however, want to avoid a hysterectomy for a variety of reasons, including plans for future childbearing, concern about the invasiveness of the procedure, the difficulty of the recuperation, or fear of diminished sexual function. Some women are simply reluctant to "give up" this part of their body so closely associated with their reproductive health, childbearing, and femininity.

Uterine prolapse can be effectively treated without hysterectomy, with low morbidity and high rates of patient satisfaction. A properly performed uterine suspension procedure often results in a significantly better anatomic outcome than a hysterectomy. Yet, many hysterectomy procedures are performed for pelvic prolapse. Many patients remain unaware of uterine-sparing options because, with the exception of a few dedicated sub-specialists, most surgeons receive no training in these techniques. Known techniques can be difficult, and can require specialized training that many general practitioners have not undertaken.

Such known techniques are complicated because implants used for uterine suspension either are formed freehand into an appropriate shape by the surgeon performing the procedure. Freehand formation or customization of implants can be difficult and is not consistently repeatable to obtain the correct size and shape.

Thus a need exists for an improved apparatus and method for providing minimally invasive procedures for repair of various pelvic dysfunctions, including uterine prolapses or hysteroceles, cystoceles, rectoceles and vaginal vault prolapse.

SUMMARY OF THE INVENTION

Apparatuses and methods for various medical procedures within a pelvic region of a patient are described herein. For example, medical apparatuses for treating uterine prolapse, vaginal vault prolapse, rectocele, and cystocele, are described herein. In one embodiment, an implant includes a first portion having a shape and configured to support a tissue within the body of a patient. Markings disposed on the first portion indicate a portion of the implant to be removed for resizing the first portion such that the first portion after the resizing has a shape substantially similar to the shape of the first portion before the resizing.

In another embodiment, a method comprises resizing an implant based on a template. A template is selected from a plurality of templates based on a measurement of a patient. In one embodiment, each template has a shape substantially similar to the shape of the implant. A portion of material of the implant is identified to be removed from the implant based on the template. The portion of material is removed from the implant based on the identifying.

BRIEF DESCRIPTION OF THE DRAWINGS

FIG. 5A is a top view of an implant, according to an embodiment of the invention.

FIGS. 5B and 5C are top views of templates, according to an embodiment of the invention.

DETAILED DESCRIPTION

Figure 1:
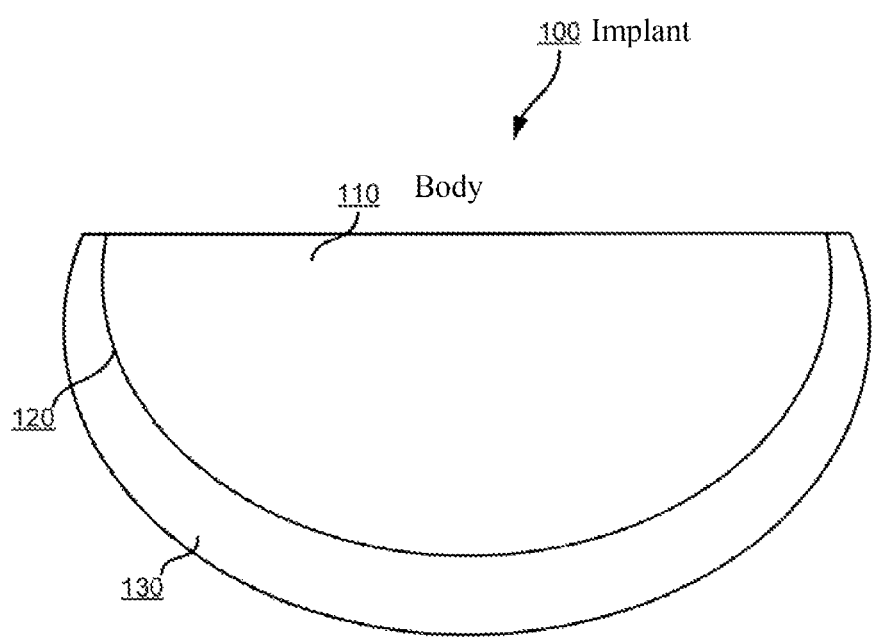
FIG. 1 is a schematic of an implant, according to an embodiment of the invention.

Apparatuses and methods for preparing an implant for various medical procedures within a pelvic region of a patient are described herein. For example, implants or implant assemblies for medical procedures to treat uterine prolapse, vaginal vault prolapse, rectocele, and cystocele, are described herein. Various implant assemblies are described herein that can be secured, for example, within a pelvic region (also referred to herein as "pelvic bowl" or "pelvic space") and used to support a prolapsed uterus. In some embodiments, the implant assemblies can be resized or customized to better suit the body of a patient. After the resizing, the implant can be inserted into the body of the patient and secured with sutures to, for example, the sacrospinous ligament, the levator muscles and/or other areas within the pelvic bowl for treating the condition. In some embodiments, the implant can also be secured to a tissue that is being supported by the implant such as, for example, the vaginal apex.

In one embodiment, an implant for treating uterine prolapse, vaginal vault prolapse, rectocele, and cystocele is pre-shaped for inserting into the body of a patient. The term "pre-shaped" is meant to distinguish shaping into a shape appropriate for insertion into the body of a patient performed prior to an implantation procedure, for example, cutting, molding, and/or other forming at a manufacturing or production facility, from shaping into a shape appropriate for insertion into the body of a specific patient performed by a doctor, surgeon, or assistant as part of an implantation procedure. The implant includes a marking such as, for example, a dashed line, indicating a portion of the implant to be removed to resize the implant for inserting into the body of a patient while maintaining the general shape of the implant. A doctor, surgeon, or person assisting in the treatment procedure removes the portion of the implant indicated by the marking by, for example, cutting along marking. Thus, the marking can help preserve the shape of the implant during resizing and provide a guide for the person performing the resizing.

In another embodiment, a pre-shaped implant for treating uterine prolapse, vaginal vault prolapse, rectocele, and cystocele is resized based on a template. A doctor or other person performing the resizing selects an appropriate template based on a measurement or dimension of a patient. The doctor then removes a portion of the implant based on the template selected. For example, a doctor can align the selected template with the implant based on the shape of the selected template and the shape of the implant and/or based on an alignment marking on the selected template and an alignment marking on the implant, and use the selected template as a guide for cutting off a portion of the implant.

In some embodiments, the shape of an entire implant is preserved during resizing. For example, a marking can run parallel to the edge of an implant such that the shape of the implant is preserved when the portion of the implant indicated by the marking is removed. In other embodiments, the shape of one portion of the implant is preserved during resizing, and the shape of another portion of the implant is not preserved during resizing. For example, an implant can have a proximal portion and a distal portion which are disproportionately resized relative one to another. The proximal portion can define a shape that is substantially preserved during resizing and the distal portion can define a shape that is not preserved during resizing. Such implants can include markings for resizing one portion of the implant more or less than another portion of the implant, and can be particularly useful for applications in which variation in patient size is greater in one dimension than in another dimension.

FIG. 1 is a schematic illustration of an implant, according to an embodiment of the invention. Implant 100 includes body 110 and marking 120. Implant 100 can be of any shape according to various embodiments and is pre-shaped for treating a condition within the body of a patient. For example, implant 100 can be pre-shaped to treat a uterine prolapse, vaginal vault prolapse, rectocele, and/or cystocele. Marking 120 defines portion 130 of implant 100 that can be removed by, for example, cutting along marking 120 to resize implant 100 for implantation. Marking 120 is configured to approximate the shape of implant 100 such that implant 100 will have a shape after portion 130 is removed substantially similar to the shape of implant 100 before portion 130 is removed.

In some embodiments, an implant can include two or more markings. For example, additional markings can be used for removing multiple portions from the implant to resize the implant to multiple sizes. In other embodiments, multiple markings can be used for removing multiple portions from various parts of an implant for resizing the implant to a desired size.

In some embodiments, additional markings can be used for removing portions of the medical implant to shape the implant to fit around or accommodate an organ or tissue. For example, an implant for treating vaginal prolapse can include a marking for removing a portion of the implant to allow a relief for the presence of a uterus. The implant can remain intact if the uterus has been removed.

In one embodiment illustrated in FIG. 1, marking 120 is a continuous line printed on implant 100. In some embodiments, a marking can be a dashed or a dotted line printed on the implant. In other embodiments, a marking can be a perforation in the implant and a portion of the implant can be removed by tearing the portion from the implant along the marking. In yet other embodiments, a marking can be a combination of, for example, a perforation and a line printed on the implant.

Implant 100 can be made from a variety of materials according to various embodiments. In some embodiments, implant 100 is made from a material that promotes tissue in-growth by, for example, including large interstices or pores in the material such that tissue can grow into the pores. In some embodiments, implant 100 is made from a material with elastic or semi-elastic properties such that implant 100 can stretch when implanted to support a tissue within the body of a patient. In some embodiments, implant 100 is made from a synthetic material such as Ployform™. In other embodiments, implant 100 is made from a natural material or tissue such as porcine, bovine (e.g., Xenform™), cadaveric (e.g., Repliform™), or other natural tissue.

Figure 2:
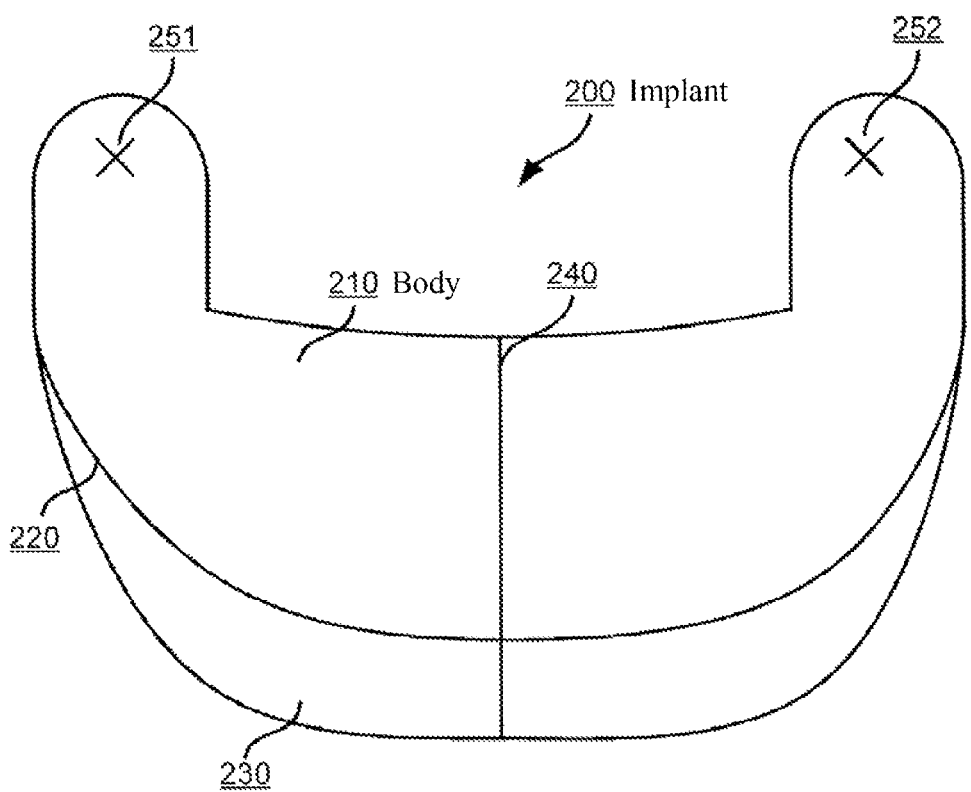
FIGS. 2-4 are top views of implants, according to other embodiments of the invention.

FIG. 2 is a top view of an implant, according to an embodiment of the invention. Implant 200 includes body 210 and marking 220 for resizing implant 200. Portion 230 of implant 200 can be removed by, for example, cutting along marking 220. In other embodiments, marking 220 is a perforation and portion 230 can be removed by tearing portion 230 from implant 200 along perforated marking 220. Implants having such perforations can be resized without the use of scissors, knives, or other sharp instruments. This can simplify the resizing procedure because fewer instruments are used and less cutting is required.

Implant 200 also includes marking 240 that indicates a center of implant 200. Marking 240 can be, for example, a solid, dotted or dashed line, a colored portion, or a pattern printed on implant 200. Marking 240 can be used to help a doctor orient implant 200 with respect to the body of a patient and/or to ensure that implant 200 is centered with respect to a tissue to be supported.

In some embodiments, an implant can include other markings for orienting and/or positioning an implant with respect to a body of a patient and/or a tissue within the body of a patient. For example, an implant can include words and/or arrows to indicate a proper orientation for inserting the implant into the body of a patient.

Implant 200 also includes markings 251 and 252 that indicate locations for attaching sutures to implant 200. Sutures can be used, for example, to attach an implant to the Sacrospinous ligament, the vaginal apex, and/or other tissues within the pelvic bowl of a patient. Markings 251 and 252 can be, for example, symbols and/or words printed on implant 200 indicating attachment points for sutures.

In some embodiments, an implant can include more or fewer markings for indicating attachment points. For example, in some embodiments, the implant includes additional markings to indicate positions at which a tissue being supported by the implant should be attached with sutures to the implant. In yet other embodiments, an implant can be attached to a tissue at locations on the implant other than those indicated by markings.

In some embodiments, implant 200 can include reinforcing materials affixed to body 210. For example, in one embodiment, body 210 has multiple layers of material proximate to markings 251 and 252 for reinforcing sutures attached to implant 200 at markings 251 and 252. Additional layers of material can be affixed to body 210 using, for example, adhesive or stitching. In some embodiments, a reinforcing material can be a material different that the material from which an implant is made. In some embodiments, reinforcing material can be affixed to other portions of an implant such as, for example, along a center of the implant and/or longitudinally and/or laterally across an implant to strengthen the implant to prevent ripping or tearing of the implant. In other embodiments, an implant can be made from a single material varying in thickness.

Figure 3:
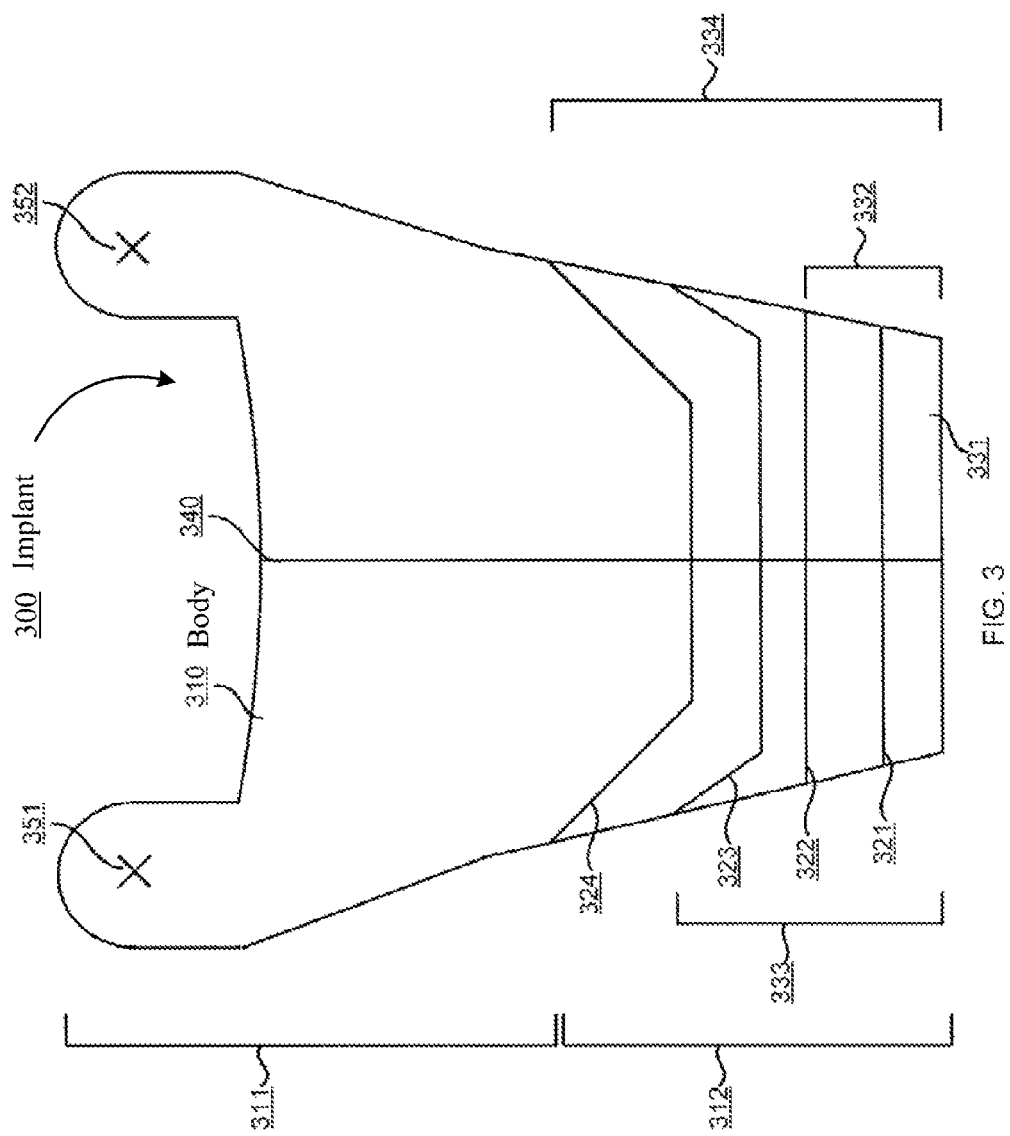

FIG. 3 is a top view of an implant, according to an embodiment of the invention. Implant 300 includes multiple markings for resizing implant 300 for insertion into the body of a patient. Upper portion 311 has a shape that is substantially preserved during resizing. The shape of lower portion 312 is not preserved during resizing. Implant 300 includes body 310, marking 340 indicating a center of implant 300, and markings 351 and 352 indicating positions for attaching sutures to implant 300. Marking 340 and markings 351 and 352 are similar to marking 240 and markings 251 and 252, respectively, which are discussed above with regard to FIG. 2.

Markings 321, 322, 323, and 324 indicate different portions to be removed from implant 300 to resize an implant based on, for example, a measurement or dimension in the pelvic bowl of a patient. Portion 331 can be removed from implant 300 by, for example, cutting along marking 321. Portion 332 can be removed from implant 300 by, for example, cutting along marking 322. Portion 333 can be removed from implant 300 by, for example, cutting along marking 323. Portion 334 can be removed from implant 300 by, for example, cutting along marking 324. In other embodiments, markings 321, 322, 323, and/or 324 can be perforations and portions 331, 332, 333, and/or 334 of implant 300 can be removed from implant 300 by tearing along markings 321, 322, 323, and/or 324. Thus, implant 300 can be configured into five different sizes, in each of which the general shape of upper portion 311 of the implant is preserved without requiring that a doctor or other person performing or assisting in the procedure make a freehand cut of the implant.

In some embodiments, an implant can include indications of a measurement or dimension and/or a range of measurements or dimensions, for example, within the pelvic bowl of a patient that are associated with each of a number of markings for resizing the implant. For example, "3-5 cm" can be printed on an implant in close proximity to a first marking on the implant for resizing the implant, and "5-7 cm" can be printed on the implant in close proximity to a second marking on the implant for resizing the implant. In other embodiments, different ranges or different measures can be printed on an implant. A doctor can measure a tissue within the pelvic bowl of a patient and cut along a first marking or a second marking based on the measurement and the ranges printed in close proximity to each marking. In other embodiments, more than two markings can be provided. Markings for resizing the implant can be of different colors, widths, styles, and/or comprised of different symbols. Instructions provided with the implant can be used to determine which marking is associated with a particular measurement or range of measurement.

Figure 4:
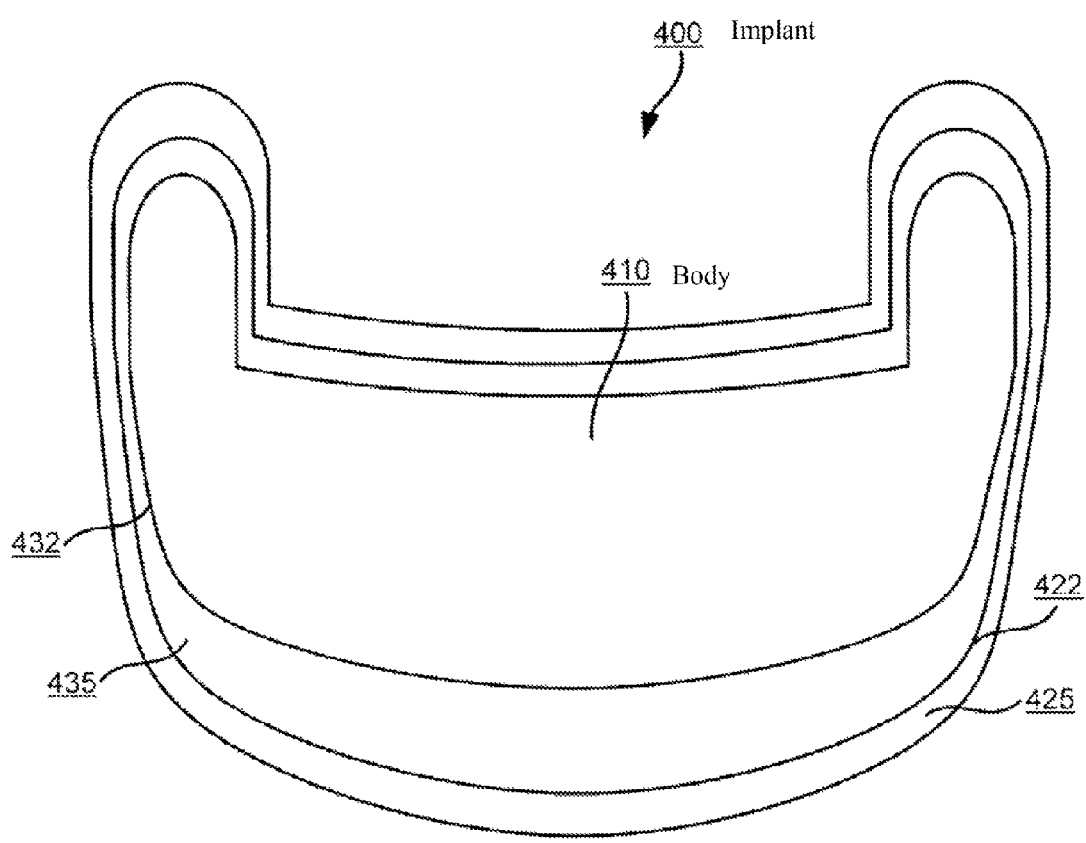

FIG. 4 is a top view of an implant, according to an embodiment of the invention. Implant 400 includes body 410 and markings 422 and 432 for resizing implant 400. Marking 422 defines peripheral portion 425 of implant 400 that can be removed from implant 400 for resizing implant 400. Similarly, marking 432 defines peripheral portion 435 of implant 400 that can be removed from implant 400 for resizing implant 400. Markings 422 and 432 each define a peripheral portion of implant 400 for removing during resizing. The distance between markings 422 and 432 varies for different portions of implant 400 to preserve the size of certain portions of implant 400. For example, markings 422 and 432 are closer one to another at tabs 441 and 442 of implant 400 than markings 422 and 432 at lower portion 443 of implant dispenser 400 to avoid removing too much material from tabs 422 and 432. In some embodiments, sutures are affixed to tabs of an implant for attaching the implant to the body of a patient. Removing too much material from the tabs of the implant can weaken the tabs such that the tabs cannot support a tissue, causing the implant to fail because of, for example, sutures tearing from tabs.

In some embodiments, an implant can be resized disproportionately in one dimension with respect to another dimension. Such embodiments can be particularly useful for supporting tissues that have more variation in size in a first dimension than in a second dimension. FIG. 4 includes axes defining an x dimension and a y dimension. Implant 400 is disproportionately resized in the y dimension with respect to the x dimension by removing peripheral portions 425 and 435 from implant 400. In other embodiments, the markings for removing various portions of an implant can be configured to preserve the proportionality of an implant such that the implant after the resizing has a shape that is a geometrically similar figure to the shape of the implant before the resizing.

FIG. 5A is a top view of an implant, according to an embodiment of the invention. FIGS. 5B and 5C are top views of an templates, according to an embodiment of the invention. Implant 510 includes alignment marking 512. Similarly, template 520 includes alignment marking 522 and template 530 includes alignment marking 532. Template 520 can be aligned with implant 510 for resizing an implant by aligning alignment marking 512 with alignment marking 522. Template 530 can similarly be aligned with implant 510 for resizing an implant by aligning alignment marking 512 with alignment marking 532.

In some embodiments, alignment markings can include single horizontal or vertical lines positioned on an implant and templates such that the implant and templates can be aligned based on the positioning and length of the lines. In other embodiments, alignment markings can be circular, oval, rectangular or other geometric shape. In some embodiments, alignment markings can be shaped to preserve orientation of the implant. For example, an alignment marking can be a non-symmetric star or other non-symmetric figure.

In other embodiments, templates can be aligned with an implant based on features or portions of the implant and/or templates. For example, tabs 514 and 515 of implant 510 can be aligned with tabs 524 and 525 of template 520. Template 530 can similarly be aligned with implant 510 based on tabs 534 and 535. In other embodiments, templates and an implant can include one or more tabs or notches for aligning the templates and the implant.

Templates 520 and 530 are similar in shape to implant 510. Implant 510 is manufactured or pre-shaped to have a shape appropriate for inserting into the body of a patient to treat a condition by, for example, supporting a tissue within the body of a patient. Template 520 and 530 are similar in shape to implant 510 to preserve the general shape of implant 510 during the resizing procedure, while changing some dimensions of implant 510 such that implant 510 better suits the body of the patient.

In some embodiments, template are made from disposable material such as, for example, paper and configured for a single use or limited number of uses. In other embodiments, templates are made from a more durable material or materials, for example, plastic, aluminum, and/or stainless steel, and are intended to be used many times. In some embodiments, templates are clear or translucent to allow viewing of an implant through the templates, for example, to aid in aligning the templates with the implant. In one embodiment, templates are included in a kit with an implant.

A doctor uses a template to resize an implant by determining or identifying an appropriate template for a particular patient. In some embodiments, each template can be associated with a particular measurement or dimension and/or range of measurements or dimensions of, for example, a measurement of a tissue in the pelvic bowl of a patient. In some embodiments, the measurement, dimension or range can be printed, engraved or otherwise indicated on the templates. In other embodiments, colors, reference numbers or symbols that are related to measurements, dimensions or ranges can be included on the templates. For example, instruction included with the templates and/or implant can provide a key for associating a color, reference number or symbol with a measurement, dimension or range. The doctor selects an appropriate template and determines a portion of the implant to remove for resizing the implant based on the template. For example, a doctor can overlay a template on an implant and remove any portion of the implant not covered by the template.

In some embodiments, a doctor removes a portion of the implant by cutting around the template. In other embodiments, a doctor can indicate a portion of the implant to be removed by marking, using, for example, a non-toxic ink, on the template around the template and then cutting along the marking.

In some embodiments, a template can include a cutting device such as a sharpened peripheral edge configured to orthogonally, or substantially orthogonally, intersect the implant when the template is aligned with the implant and cut the implant when pressed onto the implant to remove a portion of the implant. In other embodiments, a cutting device can be a wire attached to the peripheral edge of the template and configured to be heated by application of, for example, a current the wire to cut through the implant to remove a portion of the implant for resizing the implant.

In one embodiment, a medical implant includes a first portion defining a first shape and a first area and a portion configured to be removed from the first portion. The first portion is configured to support a body tissue and has a first marking. The marking indicates the portion configured to be removed from the first portion. After the portion is removed from the first portion, the first portion defines a second shape and a second area. The second shape is substantially similar to the first shape and the second area is less than the first area.

In some embodiments, the medical implant includes a second portion and a third portion extending from the first portion and configured to be coupled to a suture. In some embodiments, the marking is a non-toxic ink marking. In some embodiments, the first marking includes a perforation to allow the portion of the first portion to be removed from the first portion without cutting.

In some embodiments, the first portion has a plurality of markings. Each marking from the plurality of markings defines a portion of the first portion to be removed from the first portion. In some embodiments, the medical implant includes an indication of a dimension of a patient. The dimension is associated with the first portion after the portion is removed.

In some embodiments, the medical implant includes a fourth portion having a first shape, a first area and a first marking. The first marking indicates a portion of the fourth portion to be removed from the fourth portion. After the portion is removed, the fourth portion defines a second shape substantially similar to the first shape and a second area less than the first area.

In one embodiment, a medical implant includes a body with a shape, an area, a marking and a peripheral portion. The peripheral portion is configured to be removed from the body based on the marking. After the peripheral portion is removed, the area of the body is less than the area of the body before the peripheral portion is removed. The shape of the body after the peripheral portion is removed is substantially similar to the shape of the body before peripheral portion is removed.

In some embodiments, the medical implant includes a first portion and a second portion extending from the body and configured to be coupled to a suture. In some embodiments, the marking is a solid line. In some embodiments, the marking is a dashed line. In some embodiments, the first marking includes a perforation to allow the peripheral portion of the body to be removed from the body without cutting.

In some embodiments, the body is configured to promote tissue in-growth. In some embodiments, the medical implant includes an indication of a dimension of a patient. The dimension is associated with the body after the peripheral portion is removed.

In one embodiments, a method for preparing a medical implant for implantation in a patient includes selecting a template from one or more templates, identifying a portion of material to be removed from the implant, and removing the portion of material from the implant based on the portion identified. Each of the one or more templates has a shape substantially similar to a shape of the implant. The portion of material to be removed from the implant is identifies based on the selected template.

In some embodiments, a template is selected based on a measurement of a patient. In some embodiments, the shape of implant after the removing is substantially similar to the shape of the implant before the removing.

In some embodiments, the method includes aligning a template with the implant based on an alignment marking on the template and an alignment marking on the implant. In some embodiments, the alignment markings are non-symmetric. In some embodiments, the template is aligned with the implant based on a feature of the template and a feature of the implant.

While certain embodiments have been shown and described above, it will be understood by those skilled in the art that various changes in form and details may be made. For example, features of an implant described in relation to one embodiment of an implant can be applicable to other embodiments of an implant. Similarly, embodiments discussed in relation to resizing an implant based on marking can be applicable to resizing an implant based on templates. Additionally, markings described with respect to one or more embodiments can be used in other embodiments. Thus, it should be understood that the devices and methods described herein can include various combinations and/or sub-combinations of the components and/or features of the different embodiments described.

What is claimed is:

1. A medical implant, comprising:
   a first portion defining a first shape and a first area, the first portion being configured to support a body tissue, the first portion having a first marking, a second marking, and a third marking, the first marking indicating a portion of the first portion to be removed from the first portion such that the first portion defines a second shape and a second area, the second shape being substantially similar to the first shape, the second area being less than the first area, the first marking having a shape that is substantially similar to the first shape, the second marking indicating a centerline of the medical implant, the third marking identifying a location for placement of a suture; and
   a numerical indication of a dimension of a patient associated with the first portion after the removing.

2. The medical implant of claim 1, further comprising:
   a second portion extending from the first portion, the second portion being configured to be coupled to a suture; and
   a third portion extending from the first portion, the third portion being configured to be coupled to a suture.

3. The medical implant of claim 1, wherein the first marking is a non-toxic ink marking.

4. The medical implant of claim 1, wherein the first marking includes a perforation configured to allow the portion of the first portion to be removed from the first portion without cutting.

5. The medical implant of claim 1, wherein the portion of the first portion of the medical implant is a primary portion of the first portion of the medical implant, the first portion of the medical implant having a fourth marking, the fourth marking defining a secondary portion of the first portion of the medical implant to be removed from the first portion of the medical implant.

6. The medical implant of claim 1, further comprising a fourth portion having a first shape and a first area, the fourth portion having a first marking, the first marking of the fourth portion indicating a portion of the fourth portion to be removed from the fourth portion such that the fourth portion defines a second shape and a second area, the second shape being different from the first shape of the fourth portion, the second area of the fourth portion being less than the first area of the fourth portion.

7. A medical implant, comprising:
a body having a shape, an area, a first marking, a second marking, a perimeter, and a peripheral portion extending proximate an entire perimeter of the body, the first marking being a solid line and being continuous about an entire peripheral portion of the body, the first marking having a shape that is substantially similar to the shape of the body, the second marking identifying a location for placement of a suture,
the peripheral portion being configured to be removed from the body based on the first marking such that the area of the body after the peripheral portion is removed being less than the area of the body before the peripheral portion is removed and the shape of the body after the peripheral portion is removed being substantially similar to the shape of the body before the peripheral portion is removed.

8. The medical implant of claim 7, further comprising:
a first portion extending from the body, the first portion being configured to be coupled to a suture; and
a second portion extending from the body, the second portion being configured to be coupled to a suture.

9. The medical implant of claim 7, wherein the body is configured to promote tissue in-growth.

10. The medical implant of claim 7, further comprising an indication of a dimension of a patient associated with the body after the peripheral portion is removed.

11. The medical implant of claim 7, wherein the body includes a mid-portion disposed between a first tab portion and a second tab portion, the perimeter extending about the first tab portion, the mid-portion, and the second tab portion.

12. A method of preparing a medical implant for implantation in a patient, comprising:
selecting a first template from among a plurality of templates, each of the plurality of templates being separable from other of the plurality of templates and having a shape substantially similar to a shape of the implant;
aligning the first template with the implant;
identifying a portion of material to be removed from a first portion of the implant, the identifying being based on the first template; and
removing the portion of material from the first portion of the implant based on the identifying, the removing including cutting around an outermost perimeter of the first template.

13. The method of claim 12, wherein the selecting is based on a measurement of the patient.

14. The method of claim 12, wherein the removing includes removing the portion of material such that the shape of the implant after the removing is substantially similar to the shape of the implant before the removing.

15. The method of claim 12, wherein the aligning includes aligning an alignment marking on the first template and an alignment marking on the medical implant.

16. The method of claim 12, wherein the aligning includes aligning the first template with the medical implant based on a non-symmetric alignment marking on the template and a non-symmetric alignment marking on the medical implant.

17. The method of claim 12, further comprising aligning a template from among the plurality of templates with the medical implant based on a feature of the template and a feature of the medical implant.

18. The method of claim 12, wherein the first template includes a cutting device coupled thereto, the removing includes cutting the implant with the cutting device.

19. The method of claim 12, wherein the first template includes a cutting wire coupled to a peripheral edge of the first template, the removing includes cutting the implant by heating the cutting wire and contacting the cutting wire with the implant.

20. The method of claim 12, further including marking the implant with a non-toxic ink based on the first template.

* * * * *